United States Patent
Heidari

(10) Patent No.: US 11,912,974 B2
(45) Date of Patent: Feb. 27, 2024

(54) ASSEMBLY AND METHOD FOR SPATIOTEMPORAL CONTROL OF CHEMICAL, BIOLOGICAL, AND BIOCHEMICAL REACTIONS

(71) Applicant: Hossein Heidari, Houston, TX (US)

(72) Inventor: Hossein Heidari, Houston, TX (US)

( * ) Notice: Subject to any disclaimer, the term of this patent is extended or adjusted under 35 U.S.C. 154(b) by 0 days.

(21) Appl. No.: 17/973,244

(22) Filed: Oct. 25, 2022

(65) Prior Publication Data

US 2023/0174916 A1 Jun. 8, 2023

Related U.S. Application Data

(60) Provisional application No. 63/286,558, filed on Dec. 6, 2021.

(51) Int. Cl.
| | | |
|---|---|---|
| C12M 1/00 | | (2006.01) |
| C12M 1/12 | | (2006.01) |

(52) U.S. Cl.
CPC ............ *C12M 31/02* (2013.01); *C12M 25/00* (2013.01)

(58) Field of Classification Search
CPC ............................. C12M 31/02; C12M 25/00
USPC ................ 356/130–137, 601–624, 402–425, 356/237.1–237.6, 239.1–239.8, 246, 249
See application file for complete search history.

(56) References Cited

U.S. PATENT DOCUMENTS

| | | | | |
|---|---|---|---|---|
| 3,697,185 | A * | 10/1972 | Kassel | G01N 35/00 |
| | | | | 356/418 |
| 4,087,184 | A * | 5/1978 | Knapp | G01N 21/9027 |
| | | | | 356/239.6 |
| 6,334,842 | B1 * | 1/2002 | Hlavinka | B04B 5/0442 |
| | | | | 494/36 |
| 2008/0003668 | A1 * | 1/2008 | Uchiyama | G01N 21/645 |
| | | | | 356/417 |
| 2008/0230720 | A1 * | 9/2008 | Nielsen | G01N 21/9027 |
| | | | | 250/492.1 |

* cited by examiner

*Primary Examiner* — Tri T Ton
(74) *Attorney, Agent, or Firm* — Barry Choobin; Patent 360

(57) ABSTRACT

An assembly and method to precisely and concurrently control the concentration, release, and depletion of chemical and biochemical species in localized regions in a three-dimensional volume of material using spatially patterned light. The system includes a container for holding a material comprising photo-responsive substance; the container is mounted to a motorized rotation stage that rotates the container along the z-axis at a predetermined rate; and a projector configured to project radiations at predefined wavelengths along an r-axis into the container while the container is rotating, wherein the radiations from multiple angles intersect to form localized photoreactive regions within a volume of the material.

16 Claims, 5 Drawing Sheets

ASSEMBLY AND METHOD FOR SPATIOTEMPORAL CONTROL OF CHEMICAL, BIOLOGICAL, AND BIOCHEMICAL REACTIONS

CROSS-REFERENCE TO RELATED APPLICATIONS

This application claims priority to the U.S. provisional patent application Ser. No. 63/286,558 filed on Dec. 6, 2021, which is incorporated herein by reference in its entirety.

FIELD OF INVENTION

The present disclosure relates to an assembly and method for precise spatiotemporal control of chemical, biological, and biochemical reactions, processes, and concentrations of chemical, biological and biochemical species in the reaction using computed axial tomography (CT) techniques, and for the purpose of spatiotemporally manipulating, instructing, and programming microorganisms, living cells, and tissues, embedded or 3D printed within a volume of the surrounding material.

BACKGROUND

This section provides background information related to the present disclosure which isn't necessarily prior art.

Tissue engineering and bioprinting techniques allow us to produce complex 2D and 3D acellular structures in biocompatible and degradable matrices. They also allow us to manipulate cells and tissues in 2D (and in the case of fluid flow, 3D), using fluid flow and compartmentalized chips and assays that utilize electrochemical, mechanical, and optomechanical stimulation as well as projected 2D electromagnetic fields and acoustic waves.

The need for volumetric manipulation of cells and tissues in 3D with a spatially complex stimulation pattern has now risen with the advent of additive manufacturing processes that target large volume tissue and organ production beyond 2D. The next major step after the 3D structure is manufactured with these advanced manufacturing methods, is introducing cells into these environments and spatiotemporally stimulating and programming their development into functional tissues. This step of the process is typically overlooked as we resort to basic 2D stimulation techniques described above, or cell injection and excitation with the flow, and passive diffusion of biochemical species within these engineered perfusable matrices.

The known in vitro stimulation modalities are either 2D or require physical manipulation and stimulation of matter. The reality is that as engineered and sophisticated as the design of the manufactured matrix can be, once manufactured as a whole object neither of these physical means of stimulation allows to selectively access and manipulate an arbitrary remote location within its volume. For instance, in the case of a printed tissue model, as sophisticated as the engineered fluidic and electrical stimulation networks and arrays are by design, they cannot possibly access every remotely embedded single cell or cellular population within the volume. Furthermore, the geometrical design imposes constraints on the extent of stimulation. For example, the type and concentration of species made available at a certain location along with the fluidic transport network are shared and depends on the uptake of other points along the route as well as the diameter of the channels in that given position, and since the design is already fixed, it is impossible to actively modulate and deliver content disproportionate to the built-in geometrical form.

Thus, a need is appreciated for an improved assembly and method for spatiotemporal control of chemical, biological, and biochemical reactions.

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to an assembly and method for computed axial stimulation (CAS) that allows accessing remote cell colonies and clusters throughout a volume of a 3D matrix and trigger numerous light-induced and light-activated biochemical processes and cellular events using spatially patterned light.

It is another object of the present invention to have a whole-volume 3D spatiotemporal access to single-cell-level to tissue-level stimulation.

It is still another object of the present invention to control levels of chemical and biochemical species as well as small molecule drugs and gases in three-dimensional space or volume.

It is still another object of the present invention that the process is non-invasive and sterile.

It is yet another object of the present invention to trigger stem cell differentiation and cellular activity throughout a volume.

It is a further object of the present invention to enable fabricating multicellular bio-printed tissues and organs.

It is still a further object of the present invention to accelerate cellular stimulation.

It is an additional object of the present invention to provide high-resolution light-based processing that can handle sub-micron resolution localized excitation and stimulation.

In one aspect, disclosed is a method to precisely and concurrently control the concentration, release, and depletion of chemical and biochemical species in all or localized points in a three-dimensional volume of material using spatially patterned light. Disclosed is a method to control and manipulate chemical and biological processes i.e., the behavior of living cells and microorganisms embedded and present in a defined volume, by triggering a biological response to the spatiotemporally localized concentration changes of such chemical and biochemical species.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
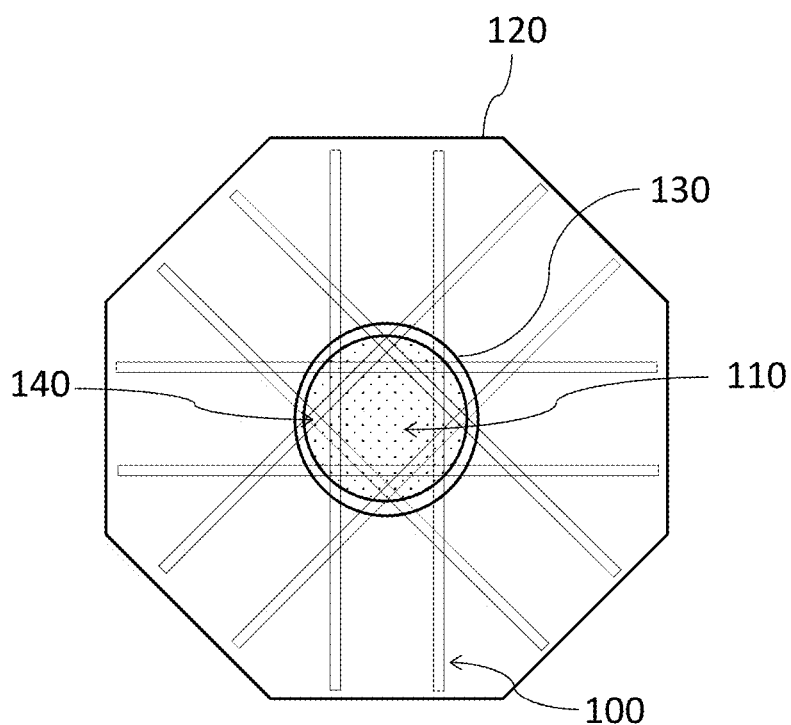
FIG. 1 is a perspective view of an assembly for spatiotemporal control of chemical, biological, and biochemical reactions, according to an exemplary embodiment of the present invention.

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention since the scope of the invention will be best defined by the allowed claims of any resulting patent.

Disclosed is an assembly and method to control the concentration, release, and depletion of chemical and biochemical species precisely and concurrently in all or localized points in a three-dimensional volume of material using spatially patterned light. Disclosed is a method to control and manipulate chemical and biological processes i.e., the behavior of living cells and microorganisms embedded and present in a defined volume, by triggering a biological response to the spatiotemporally localized concentration changes of such chemical and biochemical species. Disclosed is an assembly and method for precise spatiotemporal control of chemical, biological, and biochemical reactions, processes, and concentrations of chemical, biological and biochemical species in the reaction using computed tomography (CT) techniques, and for the purpose of spatiotemporally manipulating, instructing, and programming microorganisms, living cells, and tissues, embedded or 3D printed within a volume of the surrounding material.

Referring to FIG. 1 which shows a schematic diagram of projecting focused beams 100 axially through a volume of the material 110 in a predefined pattern. The material can be rotated around the z-axis to expose different areas within the volume of the material being exposed to the radiations. Container 130 can be rotated exposing the contents 110 within the container 130 to 2D projections 120 from the light source allowing the light in predefined patterns to irradiate targets areas within the volume of the material 110. As it can be seen in FIG. 1, the contained volume of the material can be simultaneously exposed to optical projections extending through the volume from multiple angles while the material can be rotated along the z-axis. The individual optical projections are 2D spatial intensity distributions that create a 3D intensity map based on their intersection within the volume of material. Hence, different regions 140 within the volume reach different exposure doses through a fixed exposure interval. This 3D spatial pattern of exposure energy is used to trigger certain chemical and biochemical reactions that manipulate and instruct cellular behavior via controlling the types and concentrations of chemical and biochemical species in the surrounding environment of the cells.

Figure 2:
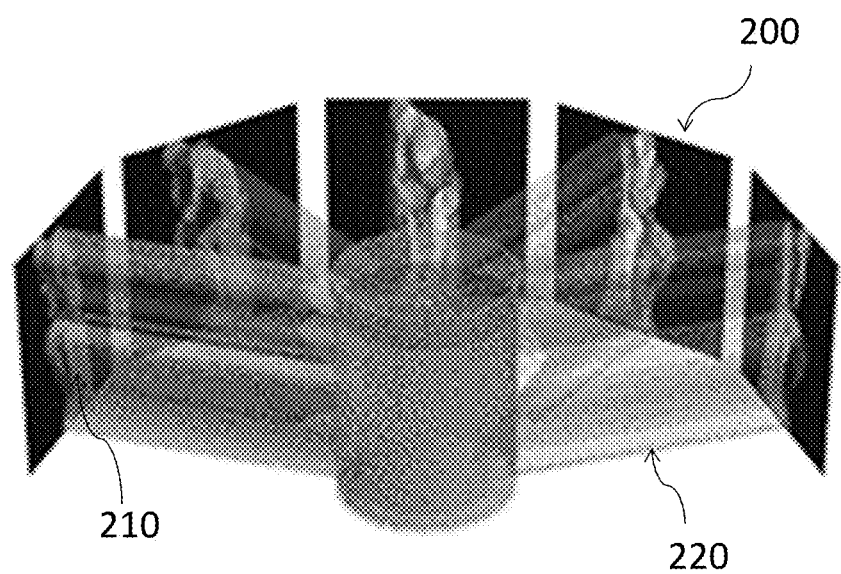
FIG. 2 shows the pattern light irradiated on the material, according to an exemplary embodiment of the present invention.

The 2D projections can be grayscale and multi-color (multi-wavelength), and light can be projected in a predefined pattern, wherein the targeted areas within the volume of material can be exposed to the projected light from the projector or other patterned illumination source. FIG. 2 shows multiple 2D projections 200 and 210 and the projected light path 220.

Figure 3:
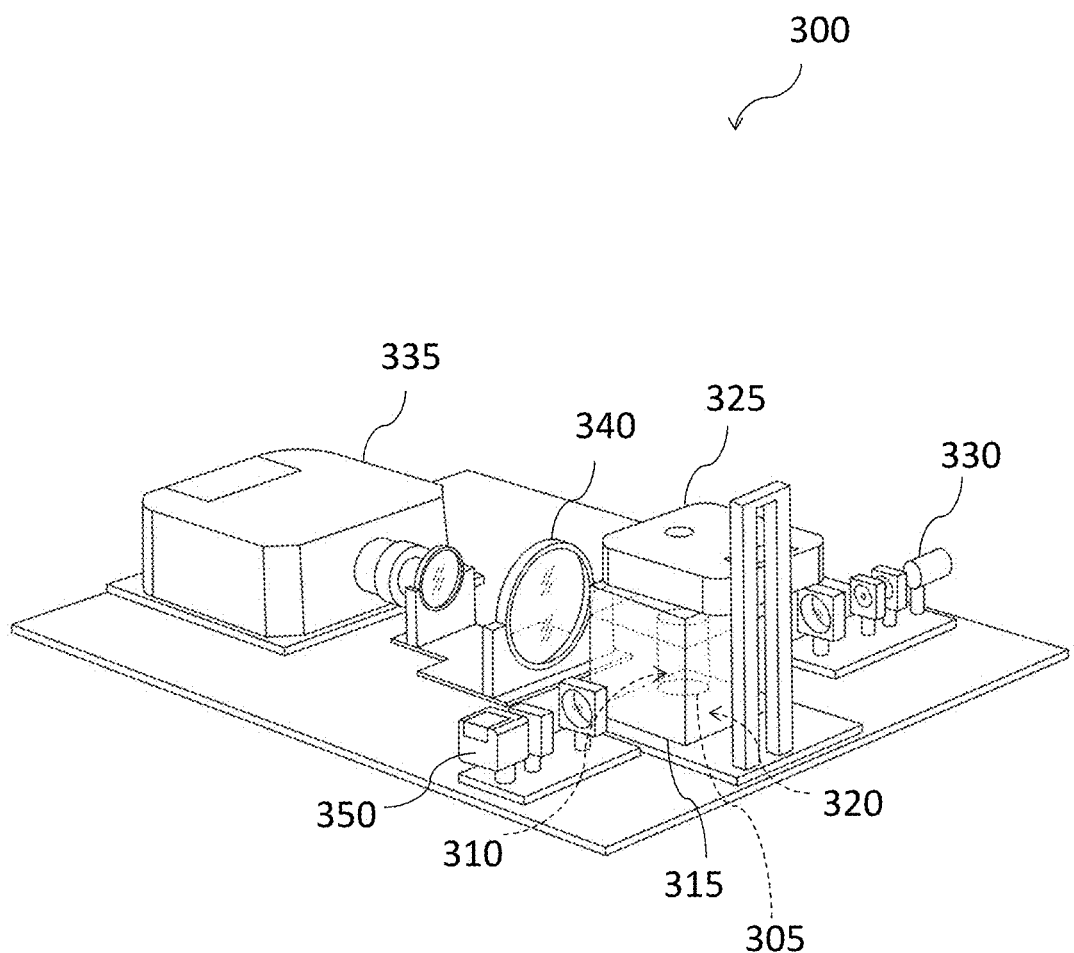
FIG. 3 is a schematic view showing the pattern light irradiation of the 3D material and point of reaction in the volume of the 3D material, according to an exemplary embodiment of the present invention.
Figure 4:
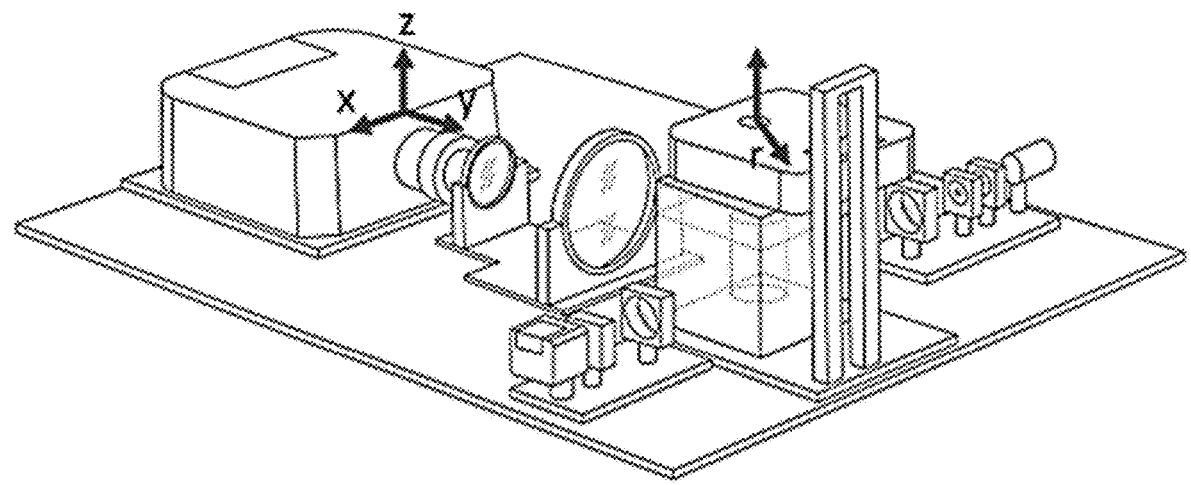
FIG. 4 is a perspective view of the assembly showing the x-axis, y-axis, and z-axis, according to an exemplary embodiment of the present invention.
Figure 5:
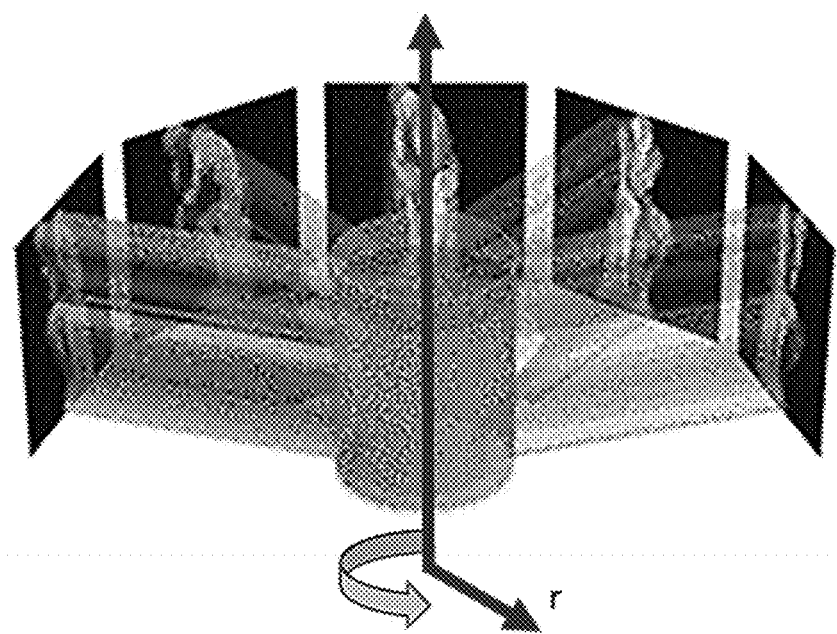
FIG. 5 shows a radial r-axis, according to an exemplary embodiment of the present invention.
Figure 6:
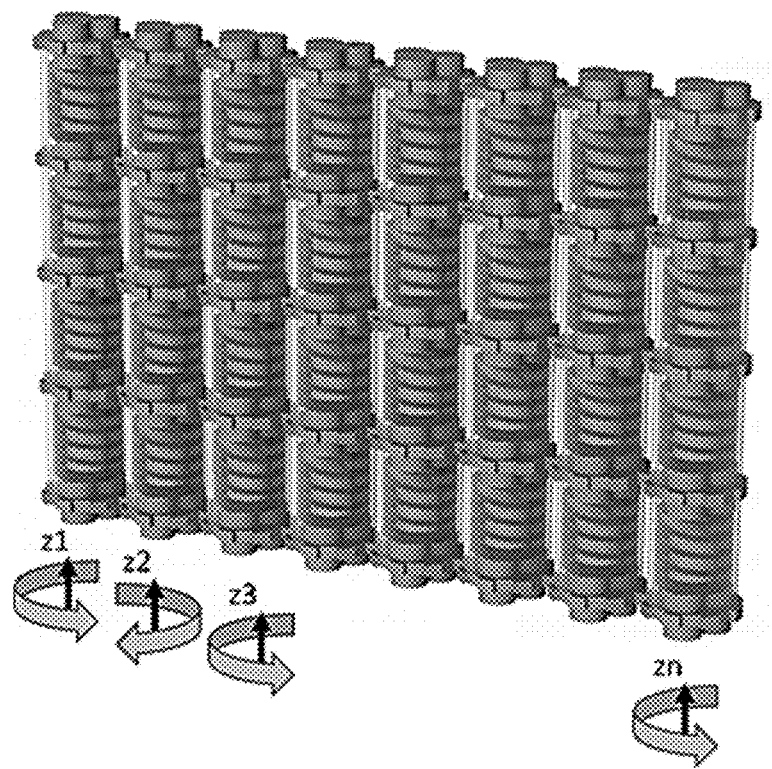
FIG. 6 illustrates multiple containers arranged in rows and columns, according to an exemplary embodiment of the present invention.

Referring to FIG. 3 which shows an exemplary embodiment of the assembly 300 according to an exemplary embodiment of the present invention. The assembly 300 includes a container 305 containing a material 310 of defined volume. Container 305 is placed within an index-matching box 315 filled with an index matching liquid 320 to keep the projected rays parallel as they travel through the volume of material. The container can be mounted to a motorized rotation stage 325 which can rotate the container and thus the material within the container at a predefined speed about the central z-axis of symmetry.

The disclosed method includes the steps of providing a volume of material contained within a container rotating about a rotation axis z with a stationary axis normal to that x. The assembly 300 can further include an optical substation 330 producing the 2D projections also stationary and its projection axis affixed to x. Alternatively, the disclosed method may include the steps of providing a volume of material contained within a stationary container while the optical subsystem that produces the 2D projections can rotate around a rotation axis z through the container and project through the contained volume in a direction axis x normal to the axis z.

The optical subsystem 330 producing the 2D projections can be a spatial light modulator (schlieren illumination source, SLM) e.g., a digital micro-mirror device (DMD), a light-emitting diode (LED) display, a liquid crystal display (LCD), a phase SLM or any other type of SLM. The operational wavelength of the optical system 325 can range anywhere from infrared to Gamma rays (including visible, UV, and X-rays). The method may include the steps of simultaneously using multiple such sources of 2D projections with different intensities, wavelengths, and projected pixel resolutions arranged at different angles about the cylindrical container.

The 2D projections from multiple angles propagate through the volume of material inside the container intersect inside the container producing a 3D map/contour of maximum light exposure dosage to trigger a biochemical or chemical reaction. Further shown in FIG. 3 is a DLP projector 335 with collimating optics 340 and an imaging system 350. The imaging system 350 can be CMOS camera sensors with proper objectives fitted with a Schlieren imaging setup. It is understood, however, that any other projectors and camera sensors are within the scope of the present invention.

In certain embodiments, the method can further include the steps of providing a means of temperature control, humidity control, and ambient gas (oxygen, nitrogen, carbon dioxide, etc.) concentration control to the material container. The assembly may include the temperature control mechanism and humidity control mechanism, and any other mechanism or system needed for the reaction and facilitate the reaction known to a skilled person are within the scope of the present invention.

The index-matching box filled with an index matching liquid surrounding the cylindrical container can keep the projected rays parallel as they travel through the volume of material. It is understood, however, that the index matching box may be replaced with cylindrical lenses or solid pieces of glass that complement the geometry of the cylindrical container.

In certain embodiments, the contained material may consist of a photoactivatable substance capable of undergoing one or multiple of the photo-activated biochemical responses. The triggered photo-activated biochemical reactions include but are not limited to the photoactivated release of caged chemical and biochemical substances such as growth factors, oligonucleotides, gene expression regulators, promoters, gene-editing proteins, genome modifying enzymes, cytokines, interleukins, interferons, necrosis factors, transcription factors, nucleobases, fluorophores, metal ions, essential gases and nutrients, proteins, vitamins, conjugated small-molecule drugs, neurotrophic and stimulating factors, biological growth inhibitors and nutrients, as well as the photoactivated suppression and inhibition of chemical and biochemical species such as adhesion ligands, gene expression regulators, growth factor receptors and other membrane receptor proteins, and RNA silencing complexes, and the photoactivated depletion of essential gases and nutrients in the environment such as oxygen, carbon dioxide, nitrogen, proteins and vitamins, and the photoactivated switching of protein complexes such as naturally light sensitive fusion proteins.

For example, such species may be caged and uncaged using the CAS process: growth factors such as vascular endothelial growth factor (VEGF), platelet-derived growth factor (PDGF), Insulin-like growth factors (IGF), neurotrophic factors such as ciliary neurotrophic factors (CNTF) and colony-stimulating factors (M-CGF), interleukins such as IL-1, IL-2, and IL-3, conjugated small molecule drugs such as antibody-drug conjugates and caged drugs, photo-switchable light-activated proteins such as LOV domains, channelrhodopsins, and protein dimerizers, and gene expression and transcriptional regulators such as triplex-forming oligonucleotides and thymidine nucleobases.

The photoremovable caging mechanisms include but are not limited to metal-organic cages including caging molecules and ligands with electrostatic interactions, hydrophobic metal-organic frameworks or tails, host-guest interaction ligands, hydrogen-bonding ligands, Van der Waals interaction ligands, and $\pi$-$\pi$ stacking ligands, as well as photocleavable and photoremovable protecting groups (PPG) including single- and multi-photon absorbing covalently bonded PPGs such as the derivatives of nitrobenzene, coumarin, cyanine, xanthene, and corrin ring containing naturally occurring vitamins.

Again, referring to FIGS. 1 and 2, multiple instances of 2D projections are shown to illustrate angular illumination in computed axial stimulation to build energy within the volume of photo-responsive material using superimposed light exposures while the material rotates respective to the light source. Thus, a single projector can project 2D projections into the container while the container is being rotated to give an overall effect as shown in FIG. 2.

In one example, the light engine used in the first demonstration was a DLP projection system used for spatial stimulation of the photo-responsive material. A DLP Lightcrafter 4500 and 4710 by Texas Instruments was used here. The light source may consist of several wavelengths for the activation of different molecular motifs. In a first demonstration 385 nm, 405 nm, and 510 nm LEDs were used with a quoted optical output power of 2.5 W. Multiple planoconvex and convex lenses and mirrors were used to collimate the light expanding from the built-in lens tube of the projector. The projector image size at the central plane of the cylindrical build volume was controlled to provide a nominal pixel size of 25-100 μm and a light intensity of 10-500 mW/cm2. Each vial was rotated about its longitudinal axis using a motorized precision rotation mount with a 3-180°/s rotation rate. The coupling of the vial with the rotation stage is achieved using a magnetic kinematic coupling mount.

The method is used to control and manipulate chemical and biological processes e.g., the behavior of living cells and microorganisms embedded and present in a 3D environment, by triggering a biological response to the spatiotemporally localized concentration changes of such chemical and biochemical species. In the schematic images below, you can see how desired localized tissue zones within the 3D volume of material can be selectively activated using the superposition of projected 2D angular light patterns.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. An assembly for spatiotemporal control of chemical, biological, and/or biochemical reactions, processes, and/or concentrations of chemical, biological, and/or biochemical species in a photoreactive volume, the assembly comprising:
   a container for holding a material comprising a photo-responsive substance;
   a motorized rotation stage, the motorized rotation stage configured to rotate the container about a z-axis at a predetermined rate;

one or more projectors configured to project patterned radiation in predefined wavelengths along a y-axis into the container while the container is rotating, wherein the y-axis is perpendicular to the z-axis, wherein the radiations from multiple angles intersect to form localized photoactivated regions within a volume of the material, wherein the container is held within an index-matching box comprising an index-matching substance configured to maintain the collimation of the projected radiations.

2. The assembly according to claim 1, wherein the assembly further comprises collimation optics positioned between the projector and the container, the collimation optics configured to result in the formation of collimated patterned light projected towards the container.

3. The assembly according to claim 1, wherein the assembly further comprises an optical substation configured to produce 2D projections projected through the container about an x-axis, wherein the x-axis is perpendicular to the y-axis and z-axis.

4. The assembly according to claim 1, wherein the assembly further comprises:
an imaging system, the imaging system further comprises an optical sensor, focusing and collimation optics, and an excitation/emission source and filters.

5. The assembly according to claim 4, wherein the imaging system further comprises a lateral light sheet illuminator that illuminates a cross-section of the container at a predefined wavelength as the excitation source for the optical imaging sensor.

6. The assembly according to claim 1, wherein the assembly further comprises multiple containers rotating about parallel z-axes and being concurrently exposed to the projected radiation.

7. The assembly according to claim 1, wherein the container is fluidically connected to the outside and is perfused with fluids throughout its rotation about the z-axis.

8. The assembly according to claim 3, wherein the 2D projections comprise a plurality of different projections that are played in a sequence.

9. The assembly according to claim 1, wherein the patterned radiation are in a form of optical projections, wherein each optical projection comprises a 2D spatial intensity distribution, and consecutive optical projections create a 3D intensity map/contour based on intersections between thereof within the volume of material.

10. An assembly for spatiotemporal control of chemical, biological, and/or biochemical reactions, processes, and/or concentrations of chemical, biological, and/or biochemical species in a photoreactive volume, the assembly comprising:
a container for holding a material comprising a photo-responsive substance;
a motorized rotation stage, the motorized rotation stage configured to rotate the container about a z-axis at a predetermined rate;
one or more projectors configured to project patterned radiation in predefined wavelengths along a y-axis into the container while the container is rotating, wherein the y-axis is perpendicular to the z-axis, wherein the radiations from multiple angles intersect to form localized photoactivated regions within a volume of the material, wherein the patterned radiation results in different regions within the volume to reach different exposure doses through a fixed exposure interval.

11. The assembly according to claim 9, wherein the rotation of the container is configured to cause 2D projections, from multiple angles, to propagate through the volume of material inside the container and intersect producing the 3D map/contour of maximum light exposure dosage to trigger a biochemical or chemical reaction.

12. The assembly according to claim 1, wherein the assembly further comprises temperature control, humidity control, and ambient gas concentration control mechanisms.

13. A method for spatiotemporal control of chemical, biological, and/or biochemical reactions, processes, and/or concentrations of chemical, biological, and/or biochemical species in a photoreactive volume, the method comprises:
providing an assembly comprises:
a container for holding a material comprising photo-responsive substance;
a motorized rotation stage configured to rotate the container about a z-axis at a predetermined rate;
one or more projectors configured to project patterned radiation in predefined wavelengths along a y-axis into the container while the container is rotating, wherein the y-axis is perpendicular to the z-axis, wherein the radiations from multiple angles intersect to form localized photoactivated regions within a volume of the material;
subjecting the container containing the material to the patterned radiation resulting in a photo-activated reaction within the material,
wherein the patterned radiation is in a form of 2D projections, each 2D projection has light zones of different intensity, wherein the patterned radiation results in different regions within the volume to reach different exposure doses through a fixed exposure interval.

14. The method of claim 13, wherein the method further comprises providing a means of temperature control, humidity control, and ambient concentration control to the material container.

15. The method of claim 13, wherein the assembly further comprises collimation optics positioned between the projector and the container, the collimation optics configured to result in the formation of collimated patterned light projected towards the container, and wherein the container is held within an index-matching box filled with an index matching substance configured to maintain the collimation of the projected radiations.

16. The method of claim 13, wherein the rotation of the container results in subjecting the material within the container to patterned light radiation from multiple angles, wherein the 2D projections propagate through the volume of material inside the container and intersect producing a 3D map/contour of maximum light exposure dosage to trigger a reaction.

* * * * *